US 7,396,923 B2

(12) United States Patent
Petit et al.

(10) Patent No.: US 7,396,923 B2
(45) Date of Patent: Jul. 8, 2008

(54) METHOD FOR THE SULFONATION OF COMPOUNDS COMPRISING FREE HYDROXYL (OH) GROUPS OR PRIMARY OR SECONDARY AMINES

(75) Inventors: Emmanuel Petit, Amiens (FR); Dulce Garcia-Papy, Morangia (FR); Véronique Barbier-Chassefiere, Gif-sur-Yvette (FR)

(73) Assignee: Organes, Tissues : Regeneration, Reparation, Remplacement- OTR3, Creteil (FR)

( * ) Notice: Subject to any disclaimer, the term of this patent is extended or adjusted under 35 U.S.C. 154(b) by 640 days.

(21) Appl. No.: 10/853,323

(22) Filed: May 25, 2004

(65) Prior Publication Data

US 2004/0242801 A1 Dec. 2, 2004

Related U.S. Application Data

(63) Continuation of application No. PCT/FR02/04095, filed on Nov. 28, 2002.

(30) Foreign Application Priority Data

Nov. 29, 2001 (FR) .................................. 01 15444

(51) Int. Cl.
*C07H 1/00* (2006.01)
*C07C 303/06* (2006.01)

(52) U.S. Cl. ............................ 536/55.3; 558/44; 558/48
(58) Field of Classification Search ................... 558/44, 558/48

See application file for complete search history.

(56) References Cited

U.S. PATENT DOCUMENTS 5,221,489 A * 6/1993 Bloys et al. .................... 524/3
5,229,504 A 7/1993 Hayashi

FOREIGN PATENT DOCUMENTS

WO WO 99/29734 6/1999

OTHER PUBLICATIONS

Toshiharu Yamada et al., Preparation and anti-HIV activity of Low-molecular-weight carrageenans and their sulfated derivatives, Carbohydrate Polymers 32(I), pp. 51-55 (1997).*

* cited by examiner

*Primary Examiner*—James O. Wilson
*Assistant Examiner*—Ebenezer Sackey
(74) *Attorney, Agent, or Firm*—DLA Piper US LLP

(57) ABSTRACT

A method for sulfonating compounds having one or more free hydroxyl functional groups and/or one or more optionally substituted primary or secondary functional groups, including treating the compounds with a complex of $SO_3$-DMF in the presence of an acid capture agent.

3 Claims, 3 Drawing Sheets

US 7,396,923 B2

METHOD FOR THE SULFONATION OF COMPOUNDS COMPRISING FREE HYDROXYL (OH) GROUPS OR PRIMARY OR SECONDARY AMINES

RELATED APPLICATION

This is a continuation of International Application No. PCT/FR02/04095, with an international filing date of Nov. 28, 2002 (WO 03/046014, published Jun. 5, 2003), which is based on French Patent Application No. 01/15444, filed Nov. 29, 2001.

TECHNICAL FIELD

This disclosure relates to a method for preparing sulfated compounds under reproducible, nondegrading conditions compatible with the uses of the compounds in which a precise molecular definition is described such as, for example, in the case of therapeutic agents. The method is broadly applicable to monomeric, oligomeric and polymeric compounds comprising free hydroxyl (OH) groups or, optionally, substituted primary or secondary amines. Our disclosure pertains more particularly to an O and N sulfonation method for functionalized polymers.

BACKGROUND

The methods for preparing sulfated compounds reported in the prior art generally induce cleavage of the chains of the polymers during the O or N sulfonation and, thus, cause the formation of potentially toxic reactional residues. It would therefore be advantageous to avoid this drawback by enabling the controlled addition of sulfonate groups under controlled conditions such that the structural integrity of the initial polymer, e.g., an oligosaccharide, is not altered.

Known in the prior art are functionalized polymers with anticoagulant properties and notably a family of derivatives obtained by substitutions on a dextran (D) chain of the carboxymethyl (CM), methyl-benzylamide (B) and methyl-benzylamide sulfonate (S) groups, designated by the abbreviation CMDBS. The methods for the preparation of these polymers were described in particular in the French Patent No. 2,461,724, as well as in U.S. Pat. No. 4,740,594. Neither of these patents provides a precise analysis of the resultant polymeric structures and the methods described do not enable providing evidence that the resultant products are homogeneous. The experimental conditions of the sulfonation reaction described in these patents promote binding of the sulfones to the free OH groups of the glucoside residue and the analysis presented does not enable the clear demonstration of the presence of benzylamine sulfonate.

Other members of the CMDBS family, designated HBGF for "Heparin Binding Growth Factor", were described as cicatrization agents in U.S. Pat. No. 5,693,625. HBFGPPs were also described for their properties of stimulating the repair and regeneration of lesions induced in muscle tissues (French Patent No. 2,718,024), nervous tissues (French Patent No. 2,718,026) and digestive tract tissues (French Patent No. 2,718,023) as well as for their anti-inflammatory properties (French Patent No. 2,718,025). These patents established a series of functional criteria for screening among all the biocompatible polymers those that respond to the following four functional properties:

protecting heparin binding growth factors (HBGFs) like the fibroblast growth factors such as FGF1 & 2 or transforming factors such as TGF-β against proteolytic degradations as well as potentiating their biological activities in a series of tests on cell cultures;

having an anticoagulant activity of less than 10 international units per mg;

inhibiting the activity of leukocyte elastase under physiological conditions; and inhibiting the activity of plasmin under physiological conditions.

French Patent Application No. 98/08309 reports the structure of a family of polymers, designated RGTA for "ReGeneraTing Agent", having the properties of the HBGFPPs and describes a method for their preparation and their properties. The RGTAs have antifibrotic effects notably enabling improvement in the quality of cutaneous cicatrices, antioxidant effects notably for treating the deleterious effects of free radicals (after ionizing radiation or during the oxidative stress induced by ischemia) and properties of regulating tissue homeostasis notably of bone masses. These properties supplement those described for the HBGFPPs.

The polymers described in French Patent Application No. 98/09309 correspond to the following formula:

$$AaXxYy \qquad (I)$$

in which:

A is a monomer; X represents an RCOOR' group; Y represents an O- or N-sulfonate group bound on A and responding to either of the following formulas: ROSO3R' or RNSO3R'; the R groups are aliphatic hydrocarbon chains optionally branched and/or unsaturated and which can contain one or more aromatic rings with the exception of benzylamine and benzylamine sulfonate; R' represents a hydrogen atom or a cation; a represents the number of monomers; x represents the level or degree of substitution of the A monomers by the X groups; y represents the level or degree of substitution of the A monomers by the Y groups.

Dextran derivatives such as CMDS are among the polymers described in French Patent Application No. 98/09309. Polymers of the CMDS type have also been described as anticoagulants (Maiga et al., Carbohydrate Polymers, 1997, 32, 89-93).

In these examples of the prior art, the synthesis methods described do not make it possible to obtain products in accordance with the criteria of sufficient reproducibility assuring the maintenance of molecular integrity and the absence of contaminants. In fact, although the methods for the substitution of carboxyl groups are widely described in the prior art and make possible controlled and managed substitution ensuring sufficient reproducibility, the sulfonation methods are more difficult to control.

The sulfonation methods are performed at a very acid pH value which does not enable preservation of the integrity of the polymer chain especially if this chain is constituted of natural sugars. Moreover, these sulfonation conditions lead to decarboxylations that are very difficult to control.

Thus, numerous studies in the prior art describe methods enabling the sulfatation of polysaccharides of type Aa. Thus, for example, dextran sulfate (or O-sulfonate) (DS), carboxymethyl dextran sulfate (CM-D-S) (or O-sulfonate) and other sulfated (or O-sulfonated) oligosaccharides such as xylan and starch were sulfated (or O-sulfonated) by methods of the type described in U.S. Pat. No. 4,814,437. Among these methods, those proposing sulfonation of polysaccharides using strong acids as sulfonation agents were reported by numerous authors. For example, U.S. Pat. Nos. 4,740,594 and 4,755,379, and French Patent No. 2,772,382 describe a treatment with chlorosulfonic acid using dichloromethane ($CH_2Cl_2$) as a solvent for the production of molecules of the CM-D-S and DM-D-B-S type. This method was already widely described in these older studies because the same acid was used for the synthesis of DS with pyridine as solvent of a basic nature (Ricketts, Biochem J, 51, 210-233, 1952). Sulfuric acid and sulfonic acid in the presence of formamide were also used for the preparation of DS at low temperatures as described in U.S. Pat. Nos. 3,498,972 and 3,141,014. It is known that these strongly acid reaction conditions induce partial degradation of the products even in the presence of solvents of a basic nature or at low temperatures. They lead to a noteworthy fragmentation of the macromolecular chain in the case of polymer products and a partial hydrolysis of certain functional groups contained in the molecules to be sulfonated. Many improvements have been introduced regarding these strong acidity conditions involving the use of better buffered media or media of lower acidity. Thus, the use of sulfur trioxide ($SO_3$) complexes as sulfonation agents less severe than sulfuric and sulfonic acids has already been introduced (Archives of Biochemistry and Biophysics, 95, 36-41, 1961; Tetrahedron Letters, 29, 7, 803-806, 1988; J. Chem. Soc. Perkin Trans. 1, 157, 1995). Many complexes of the $SO_3$ amine type have been made available commercially such as $SO_3$-$ME_3N$ (trimethylamine), $SO_3$-$Et_3N$ (triethylamine), $SO_3$-pyridine and $SO_3$-piperidine. These reagents are used in an anhydrous medium in solvents such as DMF, formamide and DMSO. Although these methods are used for the production of sulfated polysaccharides, especially those derived from dextran, functionalized by ester, ether or amid groups, they have major drawbacks because they lead to:

random fragmentation of the macromolecular chain of the polymers, albeit in lower proportions than with sulfonic acids;

partial hydrolysis of the functional groups already present on the polymers cited above; and generation of secondary products by formation of amines which contaminate the preparations and which have been shown to be toxic after inoculation in vivo (Brain Res, 16, 208-2, 473-478, 1981).

These techniques have been still further improved to eliminate to the maximum extent possible the toxic residues as well as to propose for pyridine the method described in U.S. Pat. No. 4,814,437. In fact, the $SO_3$-amines used in that method are reactive with the aldehyde groups present on the reducing end of most of the polysaccharides, notably in dextran, and the bond formed in this manner is covalent and thus permanent.

The disadvantage of the use of complexes of the $SO_3$-amine type was also overcome by employing $SO_3$-amine type complexes such as $SO_3$-DMF and $SO_3$-FA. For example, the salts of DS, more particularly the sodium salts, are presently prepared as described in U.S. Pat. No. 4,855,416 by O-sulfonation of dextran by an $SO_3$ complex associated with formamide ($SO_3$-FA) with formamide as solvent. That method comprises formation in situ of the $SO_3$-FA complex and then its reaction with dextran. The strong reactivity of the $SO_3$-FA complex induces a strong acidity of the reactional medium despite the use of an inert atmosphere ($N_2$) and anhydrous solvents. This fact also leads to the degradation of the macromolecular chain.

Another widely used non-animated complex is $SO_3$-DMF. It was in fact proposed in French Patent No. 2,772,382 for the synthesis of sulfated polysaccharides of the CM-D-S and CM-D-B-S type. However, the $SO_3$-DMF complex, like the $SO_3$-FA complex, produces a strong acidity of the reaction medium, which also leads to fragmentation of the macromolecular chain and the hydrolysis of the labile hydrolysis groups resulting in a loss of control of the synthesis and the final products. This method is thus as imperfect as the other methods in the case of the preparation of high-molecular-weight polyanionic polymers which it is not desired to cleave in a random, uncontrolled manner.

It was with this desire to improve the synthesis methods that the protocols for producing CMDBS and CMDS were described in French Patent No. 97/15702. According to French Patent Application No. 97/15702, this improvement enables on the one hand production of dextran derivatives having a greater homogeneity of molecular weight and on the other hand control of the substitution rates thus ensuring a greater homogeneity of the structures and thus a better definition. However, like the prior art, the method described in French Patent Application No. 97/15702 is based on the sulfonation of polysaccharides using an $SO_3$-amine (DMF, pyridine or triethylamine) and the examples presented are exclusively obtained with $SO_3$-pyridine. This method moreover leads to formation of residual traces of pyridine, the human toxicity of which is well known, and does not appear to enable the absence of formation of fragments of the polysaccharide chain.

SUMMARY

We provide a method for sulfonating compounds having one or more free hydroxyl functional groups and/or one or more optionally substituted primary or secondary functional groups, including treating the compounds with a complex of $SO_3$-DMF in the presence of an acid capture agent.

We also provide a method for sulfonating compounds having one or more free hydroxyl functional groups and/or one or more optionally substituted primary or secondary functional groups, including a) preparing a homogeneous solution of the compound to be sulfonated in an anhydrous solvent or cosolvent or a cosolvent composed of formamide and dimethylformamide; b) adding at ambient temperature a molar excess of an acid capture agent miscible in the cosolvent; c) rapidly adding a $SO_3$-DMF complex under agitation; d) agitating the mixture obtained for about one to about two hours at a controlled temperature below about 30° C.; and e) stopping the reaction by progressively adding the mixture to an alkaline solution and monitoring the pH such that it is not lower than about 4 to obtain salts of the compound to be sulfonated.

BRIEF DESCRIPTION OF THE DRAWINGS

Other advantages and characteristics will become apparent from the examples below regarding the implementation of our method with reference to the attached drawings in which.

DETAILED DESCRIPTION

Figure 1:
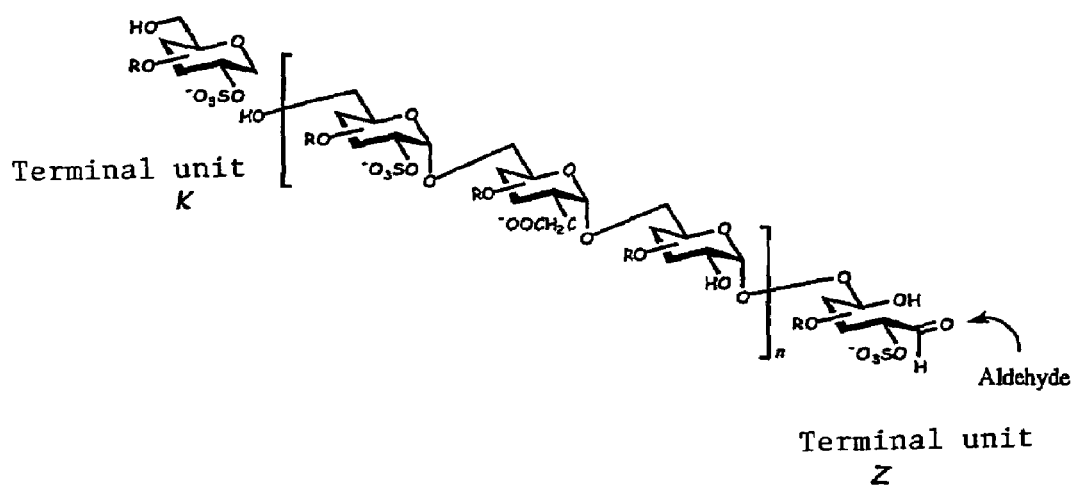
FIG. 1 is a graphic representation of a CMDS molecule in which the terminal aldehyde is shown. For a CMDS in which the values x and y are different than 0, there are three types of Z units: a) aldehyde or semiacetal, b) carboxymethyl glucoside and c) sulfonate glucoside.
Figure 2:
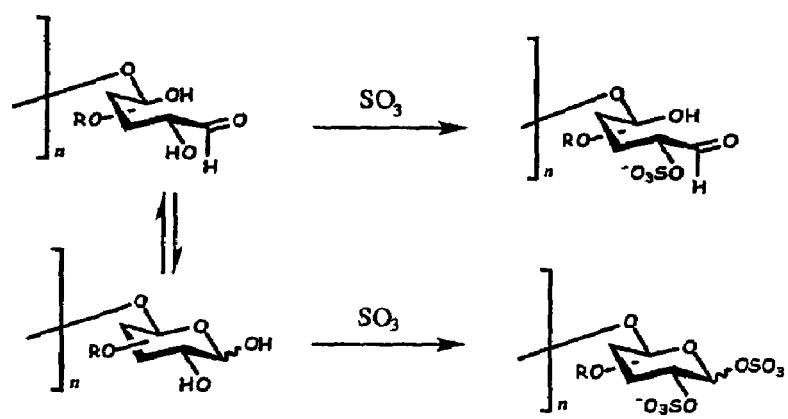
FIG. 2 shows the equilibrium between the aldehyde functional group and the semiacetal of the terminal unit of a substituted dextran. The substituted unit in anomeric position no longer participates in the equilibrium.

We provide new sulfonation methods making it possible to control with a high level of rigor and precision the conditions of the substitutions of the sulfonate groups on compounds containing hydroxyl functional group or primary or secondary amine functional groups.

This is achieved by a method for sulfonating a compound having one or more free hydroxyl functional groups and/or one or more optionally substituted primary or secondary amine functional groups comprising treatment of the compound with the $SO_3$-DMF complex in the presence of an acid capture agent.

The term "acid capture agent" means a substance or mixture of substances capable of reacting selectively with free protons in solution. After addition of the acid capture agent to a reaction medium, the protons are trapped by the acid capture agent and no longer participate in reduction of the pH value because they are no longer reactive.

The acid capture agent may be, for example, selected from the group comprising: alkenes or alkynes with a boiling point lower than about 100° C. or a mixture of these two.

The acid capture agent is preferably a butene such as 2-methyl-2-butene (2M2B), 2-methyl-propene, 2-methyl-pentene, isomers thereof or mixtures thereof.

The method is remarkable in that it makes it possible to avoid the use of excessively acidic pH values and thus substantially eliminate the risk of cleavage of the treated compounds. The method moreover has the advantage of not introducing toxic substances that are difficult or impossible to eliminate completely.

The method more particularly comprises the following steps:

a) solubilization or preparation of a homogeneous solution of the compound to be sulfonated in an anhydrous solvent or cosolvent such as dimethylformamide (DMF) or a cosolvent composed of formamide and dimethylformamide;

b) addition at ambient temperature (about 20-22° C.) of a molar excess of an acid capture agent, such as 2-methyl-2-butene, miscible in the cosolvent;

c) rapid addition of the $SO_3$-DMF complex under agitation;

d) agitation of the mixture obtained in the preceding step for one to two hours at a controlled temperature below about 30° C.; and e) stopping the reaction by progressive addition of the mixture to an alkaline solution, e.g., a 2% solution of sodium bicarbonate acid ($NaHCO_3$) or another alkali, with monitoring of the pH value such that it is not lower than about 4 to obtain the salts of the compound to be sulfonated.

The method advantageously comprises purification of the sulfonated compound obtained in step (e), e.g., by tangential ultrafiltration against water (the water being of the quality of water for human injection) via an ultrafiltration membrane at a cutoff threshold of about 1000 dalton.

The solvent employed in step (a) is preferably not dimethyl sulfoxide (DMSO) because our studies revealed that this solvent is very difficult to eliminate from the sulfonated polysaccharide preparations and thus constitutes a potential obstacle for their use in the preparation of pharmaceutical forms.

When the compound to be sulfonated is poorly soluble in an anhydrous solvent or cosolvent, a particular form of implementation of the method includes protonation of the compound to promote its solubilization. The compounds to be sulfonated are polymers of a sugar, such as dextran, substituted by one or more carboxylate groups, the protonation of which leads to formation of —COOH groups, e.g., by passage on a cation exchange column.

The sulfonation conditions are thus sufficiently managed and controlled to avoid decarboxylation of the polymer initially substituted by carboxyl groups. The sulfonation conditions are consequently advantageously the following:

The polymer to be sulfonated is dissolved in an anhydrous solvent (see, e.g., example II.1). A molar excess of acid capture agent (such as the alkene 2M2B) is added. The sulfonation reagent ($SO_3$) such as the complex $SO_3$-DMF is added and the reaction proceeds at a temperature lower than the evaporation temperature of the acid capture agent. The reaction is stopped by addition of an alkaline solution such as $NaHCO_3$.

The method is applicable to monomers, oligomers and polymers. It is most particularly suited to polymers such as the previously defined HBGFPPs and RGTAs, and thus especially to compounds derived from dextrans and copolymers of malic acids. Our disclosure thus is especially applicable to polymers of formula:

$$A_a X_x Y_y \quad (I)$$

in which:

A is a monomer; X represents an RCOOR' group; Y represents an O- or N-sulfonate group bound on A and responding to either of the following formulas: ROSO3R' or RNSO3R'; the R groups are aliphatic hydrocarbon chains optionally branched and/or unsaturated and which can contain one or more aromatic rings with the exception of benzylamine and benzylamine sulfonate; R' represents a hydrogen atom or a cation; a represents the number of monomers; x represents the level or degree of substitution of the A monomers by the X groups; y represents the level or degree of substitution of the A monomers by the Y groups.

The method can be implemented on polymers, notably those of formula (I), in which the bonds between the monomers or between the monomers and their substituents, such as the A-A or A-X bonds of the polymers of formula (I), are comprised of functional groups that are unstable in an acid medium, notably ester, amide, ether, acetal (osidic) functional groups or other groups.

The method is thus most especially suited to the preparation of monomeric or oligomeric sulfated sugars such as certain heparin fragments, or for polymers of the RGTA family notably when A is an osidic monomer as in the case of dextran-based polymers or all other polysaccharide compounds.

The following examples also comprise a comparison of the method with those of the prior art, notably for the sulfonation of polymers derived from dextran such as the CMDSs and CMDBSs. This comparison shows that the protocols proposed in French Patent Application Nos. FR 97/15702 and 99/07636 do not make it possible to obtain a good preservation of the molecular integrity of the dextran polymers because they generate fragmentations that can be detected and quantified by simple methods as well as the hydrolysis of groups grafted on the macromolecular chains.

I—Evaluation of the Sulfonation

I.1—Methods for the Measurement of the Carboxylic and Sulfonate Groups

We measured the degree of substitution (ds) of carboxyl groups (x) and sulfonate groups (y) per unit of glucose to have comparisons among the different sulfonation methods. Dextran being a glucose polymer, it possesses 3 reactive OH groups on each glucose unit. The theoretical maximum is therefore 3. The quantitative determinations were performed by titrimetric methods and by elemental analysis according to the usual protocols described in the prior art.

The titrimetric determination in combination with the elemental analysis allows determination of the global substitution rates (x and y) of the carboxymethyl ether (x) and sulfonate (y) groups.

I.2—Determination of the Position of the Substitution Groups

We used a NMR (Nuclear Magnetic Resonance of the Proton) analysis method under the standard conditions known in the art (J. Biol. Chem., 275, 38, 29383-29390, 2000). We used a Bruker 200-MHz spectrometer to be able to specify the position of the groups grafted on the osidic units.

I.3—Method for Measuring the Fragmentation of the Poly-Osidic Chains

Aldehydes present in the product in solution were determined to measure the integrity of the polymeric chain before and after the addition reaction of the sulfonate groups.

Determination of the aldehydes enabled determination of the reducing terminal units of the products because only the reducing terminal end of the polymer presents an aldehyde group as shown in FIG. 1. Thus, the number of aldehyde groups was determined on the product to be sulfonated. The number in this case is equal to 1 micromole of aldehyde per gram of product. This value must remain in all cases less than or equal to the value of the initial product if there were no formation of cleavages during the reaction.

In fact, the free aldehyde value measured after the sulfonation reaction was less than the value measured prior to the introduction of the sulfonate groups (1.0 micromole/g for a CMDS at 0.5 mmole/g). The free aldehyde values usually found for a CMDS type product in which x=0.5 and y=1.25 are close to 0.4 micromoles of aldehyde per gram of product. In contrast, if this number exceeds the initial value (1.0), there is necessarily formation of cleavages.

This method thus enables measurement of the formation of fragments because each chain cleavage generates a new detectable, reactive aldehyde.

I.4—Method for Measuring the Molecular Weights and Studying the Apparent Homogeneity of the Preparation Measurement of the molecular weights was performed by high-performance steric exclusion chromatography in 0.1 M $NaNO_3$ on columns of KB-804 and KB-805 filtration gel (Shodex Japan) in series at 0.7 ml/min. The products were detected at the column outlet by a Dawn light scattering mini-detector and a refractometer of type RID 10 (J. Biol. Chem. 275, 38, 29383-29390, 2000). the homogeneity of the preparation is reflected by the distribution curve of the molecular weights and the measurement of the width (at half height) of the peak as well as by the measurement of the symmetry of the curve.

Figure 3:
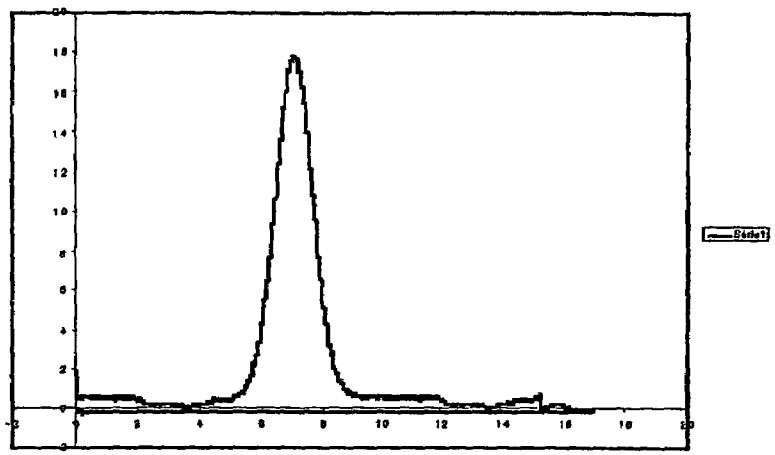
FIG. 3 shows the chromatographic profile of a type CMDS molecule with the structural characteristics described in Table 3.

A second HPLC-gel filtration technique can reveal the homogeneity of the molecule with regard to distribution of the molecular weights. A Gaussian distribution is shown in FIG. 3.

The chromatographic conditions are: Column: TSKgelG4000PWX (TOSOHAAS) at 30° C., 7.8 mm ID×30 cm; mobile phase: NaCl 0.3 M; flow rate: 0.7 ml/min; detection: IR 0.06.

It was found that for the products synthesized according to the techniques using the $SO_3$-amine complexes, homogeneity of the preparation varied according to the chromatographic system employed.

Figure 4:
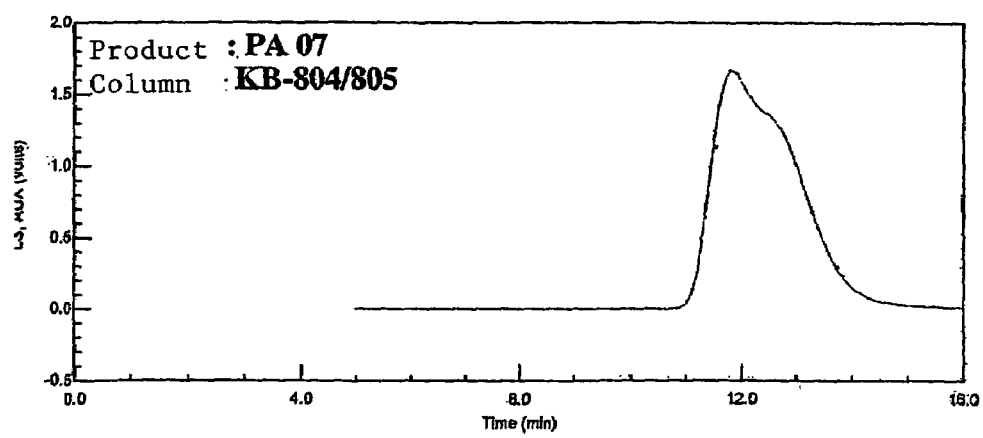
FIG. 4 shows the chromatographic profiles obtained by the same product PA 07 on different gel filtration columns.
Figure 4:
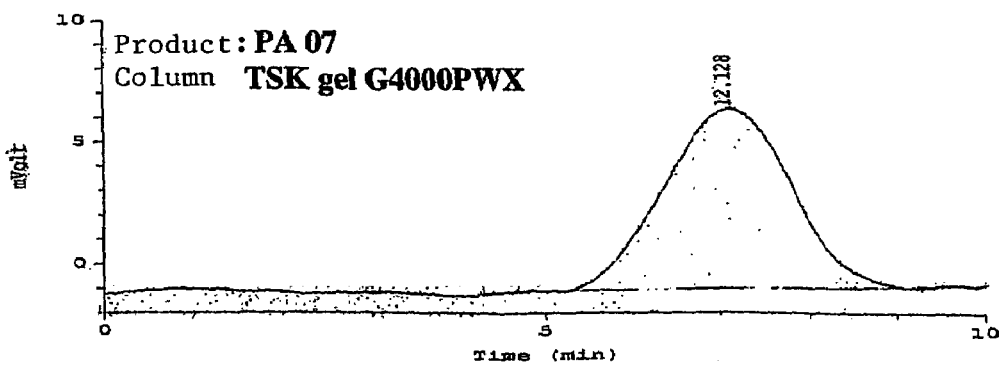
Figure 5:
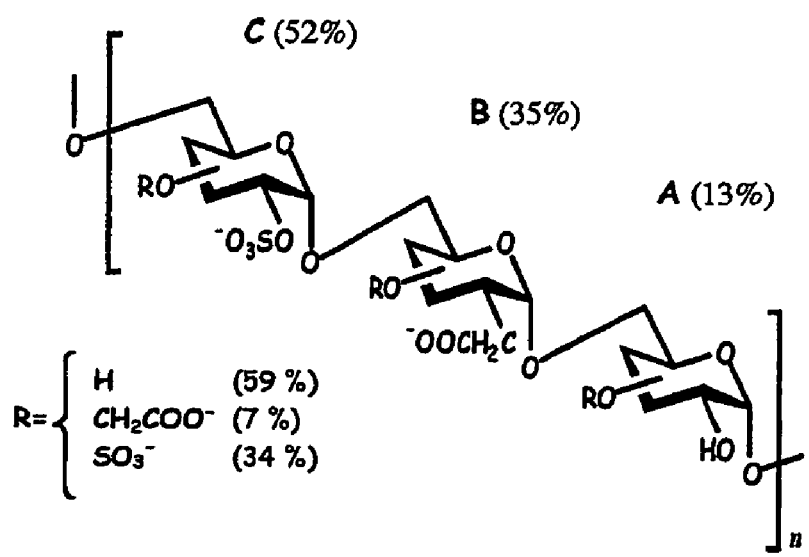
FIG. 5 shows the structure of CMDS.

When the product was separated by Shodex columns the peak was asymmetrical, but when the second chromatographic separation system was used, the peak corresponding to the same product appeared symmetrical as shown in FIG. 4. This indicates that the homogeneity of the dispersion of molecular weights in these preparations as well as those of the prior art is relative to the separation system employed.

II—Example of O-Sulfonation of Carboxymethyl Dextran Employing the Method of the Invention and in Comparison with the Prior Art II Example of O-sulfonation of carboxymethyl dextran employing our method and in comparison with the prior art Different O-sulfonation reactions by reagents such as chlorosulfonic acid, or by $SO_3$-amine complexes, the $SO_3$-DMF complex, and the $SO_3$-DMF complex in the presence of the acid capture agent 2-methyl-2-butene ($SO_3$-DMF/2M2B) are described in the examples below.

In order to establish these comparisons, carboxymethyl was selected as initial polymer.

II.1—Reaction in the Presence of the Acid Capture Agent with the Complex $SO_3$-DMF/2-Methyl-2-Butene 5 g of acid form carboxymethyl dextran (CMDH+) (24.27 mmol) was dissolved in 40 ml formamide in a 500-ml flask. Then, 40 ml of 2-methyl-2-butene (25 equivalents) was added under agitation. 7.90 g of $SO_3$-DMF (5 equivalents per unit of glucose) was added. The reaction progressed for 2 hours at 30° C. under agitation.

The reaction was stopped by very slowly pouring the reaction medium into 200 ml of $NaHCO_3$ at 2%. The pH must be close to 7. If this is not the case, the solution is neutralized by addition of soda or HCl. The pH value of the solution must never fall below 5 in any case to avoid degradation of the products.

After elimination of the excess water, the DMF and the 2M2B by rotary evaporation at reduced pressure, the product was reduced by tangential ultrafiltration followed by lyophilization. Six g of sulfonated product was obtained in the form of a white powder.

Table 1 below indicates the reproducibility of the O-sulfonation of $CMDH^+$(x=0.52) with 5 equivalents of $SO_3$-DMF and 25 equivalents of 2M2B per unit of glucose. The mean deviation (MD) percentage should be examined with regard to products prepared from the same CMD.

TABLE 1

| (x) before sulfonation | COO— in mEq/g (x) after sulfonation | mean deviation % | $SO_3$— in mEq/g (y) | mean deviation % | Aldehyde in μmol/g | mean deviation % |
|---|---|---|---|---|---|---|
| 1  0.52 | 1.58 (0.53) | 2 | 3.82 (1.28) | 5 | 0.35 | 5 |
| 2  0.52 | 1.54 (0.50) | 1 | 3.76 (1.25) | 1 | 0.49 | 3 |
| 3  0.52 | 1.57 (0.52) | 1 | 3.79 (1.26) | 1 | 0.55 | 3 |
| 4  0.52 | 1.52 (0.48) | 2 | 3.64 (1.17) | 1 | 0.60 | 8 |

Table 2 below indicates the O-sulfonation of CMDH$^+$ as a function of the quantity of reagent SO$_3$-DMF/2M2B (1:5).

TABLE 2

| SO$_3$/DMF (2M2B) | Degree of substitution (ds) | |
|---|---|---|
| equivalents per unit of glucose | x | y |
| 0.0 | 0.50 | — |
| 2.0 (10.0) | 0.49 | 0.42 |
| 2.5 (12.5) | 0.52 | 0.89 |
| 3.0 (15.0) | 0.52 | 1.00 |
| 4.0 (20.0) | 0.49 | 1.10 |
| 5.0 (25.0) | 0.52 | 1.20 |

Ten independent manipulations were performed according to this protocol: five were performed strictly following the same protocol with 5 equivalents of SO$_3$-DMF and 25 equivalents of 2M2B in accordance with Table 1, entries 1 to 4. Five others were performed while varying the amount of reagent SO$_3$-DMF/2M2B from 2 to 5 equivalents of reagent per unit of glucose. The ratio of SO$_3$-DMF to 2M2B remained constant at 1:5 (Table 2, entries 1 to 5).

The results shows that the method is reproducible for producing products possessing ether groups and osidic bonds.

In all cases, the mean deviation (MD) percentage was lower than the maximum limit set at 10%.

It should be noted that (x) does not vary significantly (MD<2%) (there is no decarboxylation) and that (y) is <3%.

The molecular weight measurements confirm the absence of heterogeneity (FIG. 3 corresponding to the product described in Table 1, entry 4) MW=67,500±7500.

The results obtained demonstrate that in the presence of 2M2B, the sulfonation rates obtained were a function of the stoichiometry of the reaction. Moreover, the reaction conditions did not affect the levels of carboxyethyl ether groups previously grafted on the CMD.

II.2—Definition of the Molecule by NMR Analysis of the Proton

Analysis of the synthesized products was performed using analytic techniques including titrimetric quantitative determination, elemental analysis, quantitative analysis of reducing sugars and HPLC/filtration on gel combined with MALLS detection supplemented by $^1$H NMR spectroscopy.

The $^1$H NMR spectroscopy provided us with the position and the ratio of the substitution rates of the different groups on the 3 reactional hydroxyls at C-2 and C-3,4 of the osidic units of the initial dextran. Table 3 below indicates the position of the X and Y substitutions on A by NMR analysis in the example type CM-D-S dextran.

OH: represents the number of OH groups not having reacted by monomer A.

d.s. is calculated from the residual hydroxyl groups not having been substituted (the initial number of free OH is 3 per monomer of glucose A; (n=3)).

C3+C4: global substitution in the positions C-3+C-4, calculated for X, Y and free OH as the difference between the total d.s. and the d.s. determined at the position C-2.

III—Comparison with the Prior Art

III.1—O-Sulfonation by Chlorosulfonic Acid. Reaction with ClSO3H

Five g of carboxymethyl dextran (24.27 mmol, one equivalent per unit of glucose) was added to 162 ml of dichloromethane. A heterogeneous mixture was obtained. The mixture was intensely agitated to obtain a homogeneous suspension of the product in dichloromethane.

1.5 ml of chlorosulfonic acid (24.27 mmol, one equivalent per unit of glucose) was slowly added to the mixture. The reaction medium was maintained under agitation for 2 hours. Agglomerates of products of a brown color formed during the reaction. The mixture was filtered (on fritted glass no. 4) and the recovered product was washed twice with 100 ml of dichloromethane, 3 times with 100 ml of a dichloromethane/dioxane (1:1) mixture and a final time with 100 ml of dioxane. The resultant product was dissolved in 200 ml of distilled water and the solution was brought to pH 9.5 by addition of soda at 2 M and then pH 7 by addition of HCl at 0.05 mol/l.

The solution was filtered, concentrated and precipitated by 500 ml of methanol. The resultant precipitate was then dried in an oven prior to being purified.

Three independent manipulations were performed according to this protocol:
one with one equivalent of chlorosulfonic acid at ambient temperature;
one with two equivalents of chlorosulfonic acid at ambient temperature; and
one with two equivalents of chlorosulfonic acid at 4° C.

III.2—Reaction with SO3-Amine and Amide Complexes

The protocols outlined above were implemented using different complexes based on SO3: SO3-pyridine, SO3-trimethylamine, SO3-triethylamine and SO3-DMF (dimethyl formamide).

Table 4 below indicates the structural and biological characteristics of the products obtained by O-sulfonation of a CMD (d.s. C=0.56) by the different complexes of SO3.

In a 500-ml flask, 5 g of carboxymethyl dextran (24.27 mmol, one equivalent per unit of glucose) was dissolved in 50 ml of formamide. To promote the dissolution of the car-

TABLE 3

| | ds | | | Positions of the groups Expressed in ds | | | | Molecular weight |
|---|---|---|---|---|---|---|---|---|
| | | | | X | | Y | | |
| Polymer | X | Y | OH | C2 | C3 + C4 | C2 | C3 + C4 | |
| CMDS | 0.50 ± 0.4 | 1.20 ± 0.4 | 1.30 ± 0.4 | 0.35 | 0.15 | 0.52 | 0.68 | 67,000 ± 5,000 | d.s.: Degree of substitution for each group per unit of glucose (A).
X = CM: CH$_2$COONa;
Y = SO$_3$Na.

boxymethyl dextran, the temperature of the reaction medium was brought to 50° C. Once the product was solubilized, the solution was brought to ambient temperature. For each reaction performed, a solution containing each of the complexes shown in Table 4 below was prepared independently in 50 ml of formamide and with the addition of the carboxymethyl dextran solution under agitation. The reaction advanced for 2 h at ambient temperature.

The reaction was stopped by adding 2 l of distilled water at 4° C. Mixing was performed and the pH of the medium was brought to 7.5-8 by the addition of a NaOH 2M solution.

After elimination of the excess water by rotary evaporation at reduced pressure the product was purified by tangential ultrafiltration followed by lyophilization. Six g of sulfated product was obtained in the form of a white powder.

Four independent manipulations were performed according to this protocol:
one with two equivalents of SO3-pyridine complex at ambient temperature;
one with two equivalents of SO3-trimethylamine complex at ambient temperature;
one with two equivalents of SO3-triethylamine complex at ambient temperature; and
one with two equivalents of SO3-DMF complex at ambient temperature.

Furthermore, a reaction (Table 4, line 8) was performed precisely according to the protocol described in Example 5 of French Patent Application No. FR 97/15702, in which solubilization of CMD was obtained by formation of trimethylammonium salts. The SO3-pyridine in a complex molar ratio of free OH equal to 0.4 (which corresponds to 2 equivalents of complex per unit of glucose) was dissolved in DMSO and added to the polymer solution. The reaction was carried out in dimethylformamide at ambient temperature.

Table 4 shows the structural characteristics of various polymers of type CMDS synthesized according to the different methods and the constraints of each method. The method corresponds to entries 10 and 11 of Table 4 and the conditions described in Example 1.

carboxyl groups (dsC or x) and a degradation of the macromolecular chain (molecular weight and quantitative determination of the reducing sugars). This cleavage becomes more pronounced as the number of reagent equivalents added is increased. Reduction of the temperature of the reaction medium can limit this degradation.

It should be noted that the product prepared by the complex $SO_3$-$Et_3N$ (Table 4, entry 6) was the most sulfonated product but also the product having undergone the greatest decarboxylation. This tendency was confirmed by the other products.

The last two entries of Table 4 (entries 10 and 11) employed the product 2M2B which acts as an acid capture agent to limit degradation of the ether bonds of the grafted carboxylate groups and of the macromolecular chain and degradation of the chain.

It should be noted that in the presence of the product 2M2B the dsC of the product obtained after sulfonation was identical to that of the precursor dsC. This was the case irrespective of the amount of reagent added. In fact, with 2.5 times more of complex $SO_3$-DMF (entry 11), we obtained a higher dsS, but above all the dsC did not change. The efficacy of the protocol of 2M2B is thereby demonstrated.

Whereas for the previously known O-sulfonation techniques there is decarboxylation and degradation of the macromolecular chain, the O-sulfonation technique in the presence of the product 2M2B makes it possible to resolve the problem of the loss of the carboxylate groups grafted on the dextran.

Measurements of in vivo activities as well as in vivo toxicity were performed on muscle regeneration models of the muscle extensor digitorum longus of the rear paw of the adult rat after crushing according to the experimental conditions described in Gautron J., Kedzia C., Husmann I. and Barritault D. "Acceleration of the regeneration of an adult rat skeletal muscle by dextran derivatives", C. R. Acad. Sc. Paris, Sciences de la Vie (1995), 318: 671-676. Regeneration is quan-

TABLE 4

| Sulfonation reaction | Reaction conditions | x | y | Terminal aldehyde (µmol/g) | Activity (in vivo) | Toxicity (in vivo) |
|---|---|---|---|---|---|---|
| 1 — | — | 0.56 | 0.0 | 1.00 | (−) | (−) |
| 2 ClSO3H | 1 eq/22° C. | 0.41 | 0.22 | 12.7 | variable | variable |
| 3 ClSO3H | 2 eq/22° C. | 0.37 | 0.35 | 11.0 | variable | variable |
| 4 ClSO3H | 2 eq/4° C. | 0.51 | 0.35 | 4.0 | variable | variable |
| 5 SO3-Me3N | 2 eq/22° C. | 0.50 | 0.00 | 1.9 | (+) | (+) |
| 6 SO3-Et3N | 2 eq/22° C. | 0.29 | 0.40 | 1.6 | (+) | (+) |
| 7 SO3-pyridine | 2 eq/22° C. | 0.44 | 0.17 | 1.8 | (+) | (+) |
| 8 SO3-pyridine | 2 eq/22° C. | 1.00* | 0.35 | 1.9 | (−) | (−) |
| 9 SO3-DMF | 2 eq/22° C. | 0.37 | 0.23 | 1.5 | n.d. | n.d. |
| 10 SO3-DMF/2M2B | 2 eq/22° C. | 0.57 | 0.62 | 0.8 | (+) | ( ) |
| 11 SO3-DMF/2M2B | 5 eg/22° C. | 0.55 | 1.15 | 0.5 | (+) | ( ) | n.d. = not determined
*the initial product of this experiment was substituted in CM at 1 residue per unit of glucose.

The different products of the DCS type were synthesized from a single batch of carboxylated dextran (Table 4, entry 1) with a degree of substitution in carboxylate of x=0.56. After their purification, the products were characterized by the different structural analysis techniques.

The titrimetric results showed that the O-sulfonation reactions by chlorosulfuric acid and the $SO_3$-amide or amine complexes induced a cleavage of the ether bond of the grafted tified on histological sections by measurement of the number of regenerated muscle fibers. Toxicity was measured by a diminishment of the formation of fibers (compared to the controls injected by a solution of physiological serum) as well as by analysis of the appearance of regeneration and revelation of abnormal zones of regeneration or formation of abnormal zones or formation of inflammatory zones showing a degeneration of the muscle tissues.

IV—Generalization of the method for other types of polymers

Table 5 shows the synthesis of various polymers of formula AaXxYy, in which A is a sugar and a is greater than 1, by the method and their analytic characteristics.

TABLE 5

| Initial product$_{dsC}$ | Scale | dsS | dsC | Terminal aldehyde (μmol/g) |
|---|---|---|---|---|
| 1 Dextran (D) | 2 g | 1.19 | — | 0.15 |
| 2 D | 2 g | 1.24 | — | 0.15 |
| 3 CM$_{50}$-D | 2 g | 1.22 | 0.5 | 0.20 |
| 4 CM$_{50}$-cellulose (C) | 2 g | 1.23 | 0.5 | 0.20 |
| 5 CM$_{50}$-D | 10 g | 1.17 | 0.5 | 0.20 |
| 6 CM$_{50}$-C | 10 g | 1.22 | 0.5 | 0.20 |
| 7 CM$_{60}$-B$_{60}$-D | 50 g | 1.24 | 0.5 | 0.20 |
| 8 CM$_{60}$-B$_{20}$-C | 10 g | 1.23 | 0.6 | 0.05 |
| 9 CM$_{60}$-PhA$_{60}$-D | 10 g | 1.23 | 0.6 | 0.05 |
| 10 CM$_{60}$-PhA$_{60}$-C | 10 g | 1.22 | 0.6 | 0.05 |

The invention claimed is:

1. A method for sulfonating polysaccharide compounds comprising treating the polysaccharide compounds with SO$_3$-DMF in the presence of an acid capture agent.

2. The method according to claim 1, wherein the acid capture agent is selected from the group consisting of alkenes with boiling points below about 100° C., alkynes with boiling points below about 100° C. and mixtures thereof.

3. The method according to claim 1, wherein the acid capture agent is selected from the group consisting of 2-methyl-2-butene (2M2B), 2-methyl-propene, 2-methyl-pentene, isomers thereof and mixtures thereof.

* * * * *